United States Patent
Bergeron

(10) Patent No.: US 6,524,337 B1
(45) Date of Patent: Feb. 25, 2003

(54) INTRALUMINAL PROSTHESES AND BALLOONS FOR THE ANGIOPLASTY OF ANEURYSMS

(76) Inventor: Patrice Bergeron, 38, boulevard Leï Roure, 13009 Marseilles (FR)

(*) Notice: Subject to any disclaimer, the term of this patent is extended or adjusted under 35 U.S.C. 154(b) by 0 days.

(21) Appl. No.: 09/528,084

(22) Filed: Mar. 17, 2000

Related U.S. Application Data

(63) Continuation of application No. PCT/FR98/02014, filed on Sep. 21, 1998.

(30) Foreign Application Priority Data

Sep. 19, 1997 (FR) .............................. 97 11719

(51) Int. Cl.$^7$ .................................. A61F 2/06
(52) U.S. Cl. ................ 623/1.37; 623/1.11; 623/1.13
(58) Field of Search ................ 623/1.11, 1.3, 623/108, 1.37, 1.13; 606/190, 194, 198, 200

(56) References Cited

U.S. PATENT DOCUMENTS

| | | | |
|---|---|---|---|
| 5,360,443 A | * | 11/1994 | Barone et al. |
| 5,443,498 A | * | 8/1995 | Fontaine .................... 623/1 |
| 5,843,158 A | * | 12/1998 | Lenker et al. |
| 5,893,887 A | * | 4/1999 | Jayaraman ............... 623/1.15 |
| 6,013,093 A | * | 1/2000 | Nott et al. ................ 606/200 |
| 6,264,682 B1 | * | 7/2001 | Wilson et al. ........... 623/1.11 |

FOREIGN PATENT DOCUMENTS

| | | |
|---|---|---|
| EP | 0 479 557 A1 | 4/1992 |
| WO | WO 96/28116 | 9/1996 |

* cited by examiner

*Primary Examiner*—David O. Reip
(74) *Attorney, Agent, or Firm*—Schander Harrison Segal & Lewis LLP

(57) ABSTRACT

An endoprosthesis for angioplasty of a vessel injured by an aneurysm wherein the vessel intersects another vessel and has an intersection point which forms right angles between axial lines extending through the vessels and wherein the vessel has a neck portion extending from the another vessel including an expandable frame covered by an impermeable material and having a beveled end adapted to engage the neck portion, wherein an angle of the beveled end is determined such that a front plane of the beveled end is substantially perpendicular to the axial line of the vessel at the intersection point.

7 Claims, 3 Drawing Sheets

INTRALUMINAL PROSTHESES AND BALLOONS FOR THE ANGIOPLASTY OF ANEURYSMS

RELATED APPLICATION

This is a continuation of International Application No. PCT/FR98/02014, with an international filing date of Sep. 21, 1998, which is based on French Patent Application No. 97/11719, filed Sep. 19, 1997.

FIELD OF THE INVENTION

This invention relates to apparatus for the angioplasty of aneurysms, especially aneurysms of the aorta, for which the superior neck is short. The invention particularly relates to intraluminal prostheses for implementing of angioplasty of aneurysms, as well as balloons for the expansion of such prostheses.

BACKGROUND

In the current state of the art, a prosthesis of expandable cylindrical form is introduced at the level of the aneurysm. The endoprosthesis is formed by an expandable frame made, for example, of a mesh of metal wires, covered by a material that ensures impermeability, for example, made of DACRON (trade name) or polytetrafluoroethylene (PTFE). It ensures the continuity of blood flow between the vascular parts not injured by the aneurysm, and is supported upstream and downstream of the aneurysm on the interior wall of the neck.

The prostheses of the prior art are well adapted to situations in which the superior neck is straight and sufficiently long. The contact surface of the endoprosthesis with the healthy vascular parts is then sufficient to avoid leaks (see FIG. 1).

In contrast, the prostheses of the prior art are poorly adapted to situations in which the neck is short or oblique. In such cases, the connection between the endoprosthesis and the healthy vascular part is insufficient and leaks can occur, especially at the level of the superior neck. These defects have the tendency to worsen with time, because of possible sliding of the prosthesis or in the case of aggravation of the aneurysm. Thus, it would be highly advantageous to resolve this drawback of the prior art.

SUMMARY OF THE INVENTION

The invention concerns an angioplasty process for vessels injured by an aneurysm, including introducing at the level of the aneurysm an endoprosthesis formed by an expandable frame covered by an impermeable material and then implementing expansion of the endoprosthesis after positioning at the level of the aneurysm by means of a balloon catheter, characterized in that the endoprosthesis has a beveled end that is positioned at the level of the neck, with the front plane of the beveled end such that the front plane is essentially perpendicular to the aortic axis into which the endoprosthesis opens.

According to an embodiment intended for the repair of an iliac aneurysm, an iliac prosthesis is expanded by means of a balloon configured so as to exhibit asymmetrical inflation, advantageously by means of a balloon of general cylindrical form extended at one of its ends by a divergent part.

The invention also concerns an endoprosthesis formed by an expandable frame covered by an impermeable material for the angioplasty of a vessel injured by an aneurysm, characterized in that it has a cylindrical form on one end of which is beveled so as to be positioned at the level of a short and/or oblique neck in a manner such that the front plane of the beveled end is essentially perpendicular to the median axis of the inter-renal aorta.

Advantageously, the beveled end has a front plane forming with the median axis an angle comprised between about 15 and about 40 degrees.

BRIEF DESCRIPTION OF THE DRAWINGS

A better understanding of the invention will be attained by reading the description below with reference to the attached drawings in which.

DETAILED DESCRIPTION OF THE INVENTION

Figure 3:
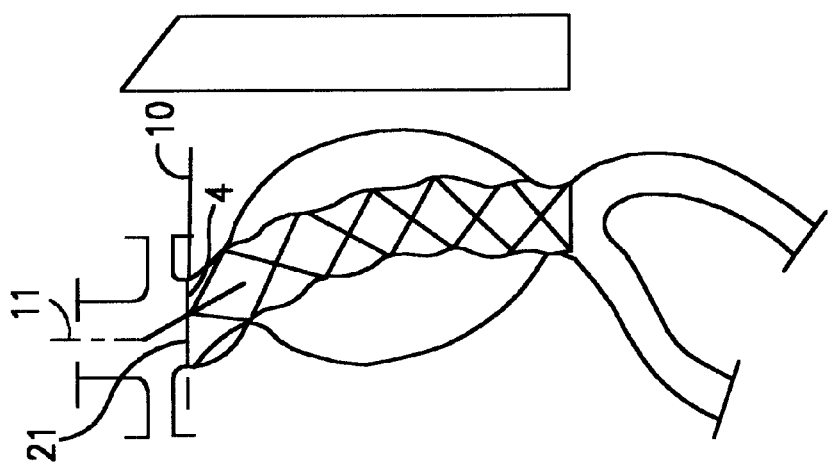
FIG. 3 is a schematic sectional view of an aneurysm with an endoprosthesis according to the invention.

The following description is intended to refer to specific embodiments of the invention illustrated in the drawings and is not intended to define or limit the invention, other than in the appended claims. Also, the drawings are not to scale and various dimensions and proportions are contemplated.

Figure 2:
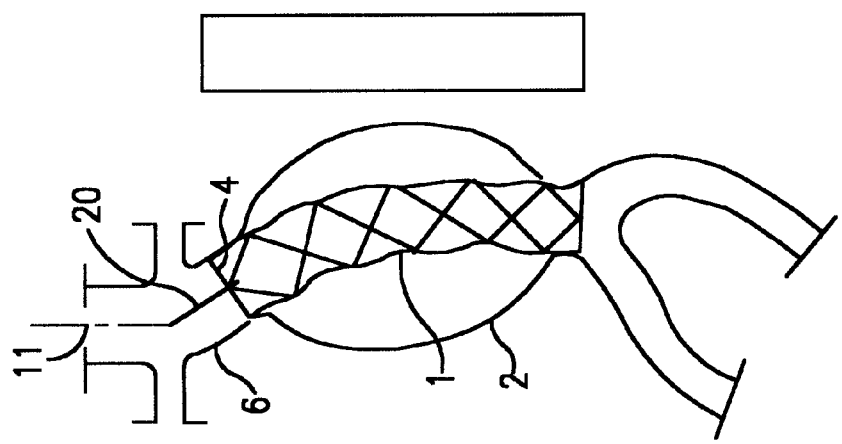
FIG. 2 is a schematic sectional view of an angioplasty technique from the state of the art for cases in which the neck is oblique.
Figure 1:
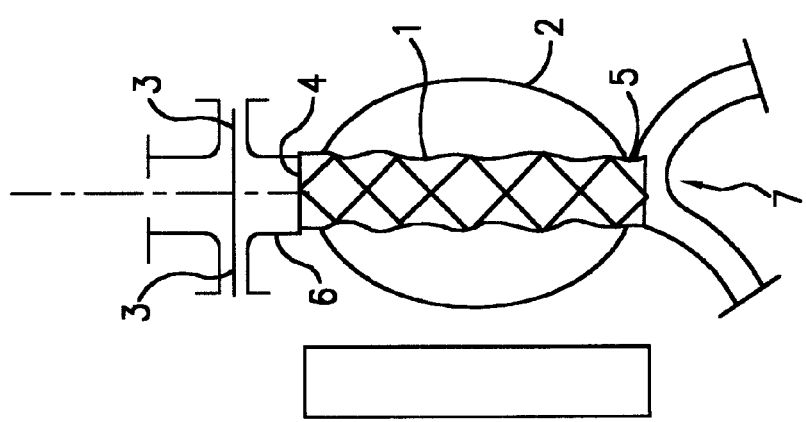
FIG. 1 is a schematic sectional view of an angioplasty technique from the state of the art.

Turning to FIGS. 1 and 2, wherein aspects of the prior art are shown, the prosthesis (1) is formed by a tubular section, the upper part of which is expandable. It has an expandable frame made, for example, of steel, embedded in a tubular envelope made of PTFE and ensuring impermeability. The endoprosthesis (1) is led through the aorta into the aneurysm (2), with one of the ends (4) of the prosthesis being positioned in the neck (6) just below the renal arteries (3), and the other end (5) being positioned above the aortic bifurcation (7).

At this time the endoprosthesis (1) is expanded by applying pressure from a balloon. The balloon is then withdrawn, leaving the endoprosthesis (1) in the aneurysm (2). The blood flow passes through the impermeable endoprosthesis (1) at the level of the aneurysm (2). The aneurysm is then isolated from the blood pressure and can in certain cases be naturally resorbed. In some cases, however, the neck (6) is short or strongly oblique as shown in FIG. 2. In this case, the contact zone between the end (4) of the endoprosthesis (1), according to the prior art, and the exterior side of the curve of the neck (6) is very short and causes poor holding of the endoprosthesis (1). If this contact zone is insufficient then local leaks can occur. This risk is especially large since the aneurysm can evolve and increase in size, thereby further reducing the quality of the contact with the end (4) of the neck (6).

FIG. 3 shows a sectional view of an endoprosthesis according to the invention. The end (4) of the endoprosthesis (1) is beveled to provide better coverage of the exterior wall of the curve and improve the holding on the neck (6). Leaks are thereby diminished. The axis (20) of the neck of the aneurysm is not always in the prolongation of the median axis (11) of the inter-renal aorta as shown in FIG. 2. These two axes frequently form an angle of several degrees with each other. The invention compensates for this angle by means of an end which is beveled according to an angle such that the front plane (10) is perpendicular not to the median axis (20) of the neck and, thus of the endoprosthesis, but rather to the median axis (11) of the suprarenal aorta.

The front plane (10) of the end of the endoprosthesis is substantially perpendicular to the median axis (11) of the inter-renal aorta, or more precisely to the tangent of the median line of neck (6) and forms with the longitudinal axis of the endoprosthesis of an angle of about 30°.

FIGS. 4–7 concern the installation of beveled endoprostheses installed on the iliac arteries at the level of an aortic bifurcation (7). The objective is to ensure good deployment of an endoprosthesis when it is deployed in the aorta, i.e., that there is no support for the balloon which is dimensioned to the size of the iliac and not to the aorta.

Figure 4:
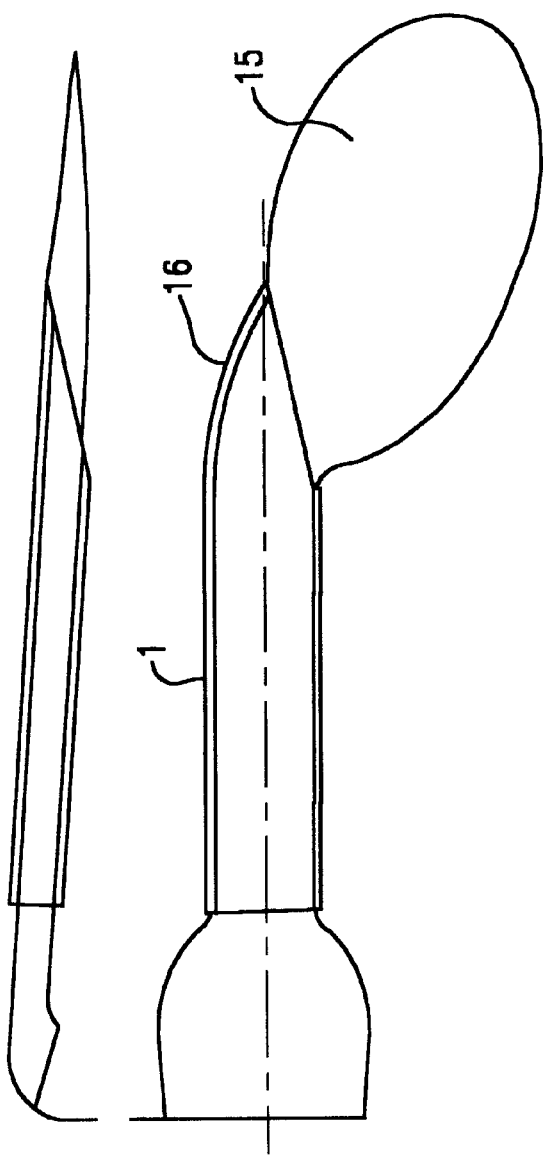
FIG. 4 is a schematic sectional view of a branched endoprosthesis implanted at the iliac level during expansion with a balloon of the prior art.

FIG. 4 shows a sectional view of an endoprosthesis during expansion with a balloon of the prior art. It can be seen that when used with an endoprosthesis with a beveled end, such a balloon (15) does not enable satisfactory deployment of the beveled end (16). The balloon is deformed due to lack of support on the beveled part (16) and causes a parasitic curve of the end of the prosthesis.

Figure 5:
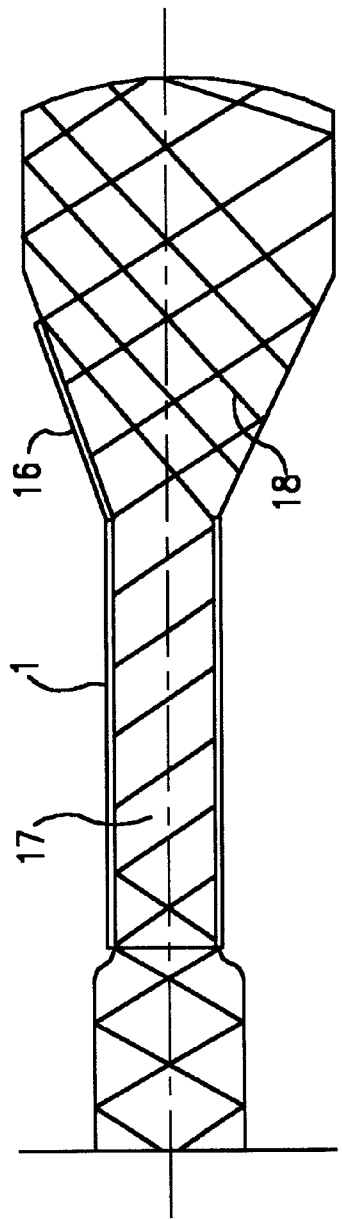
FIG. 5 is a schematic sectional view of an endoprosthesis during expansion with a balloon according to the invention.
Figure 6:
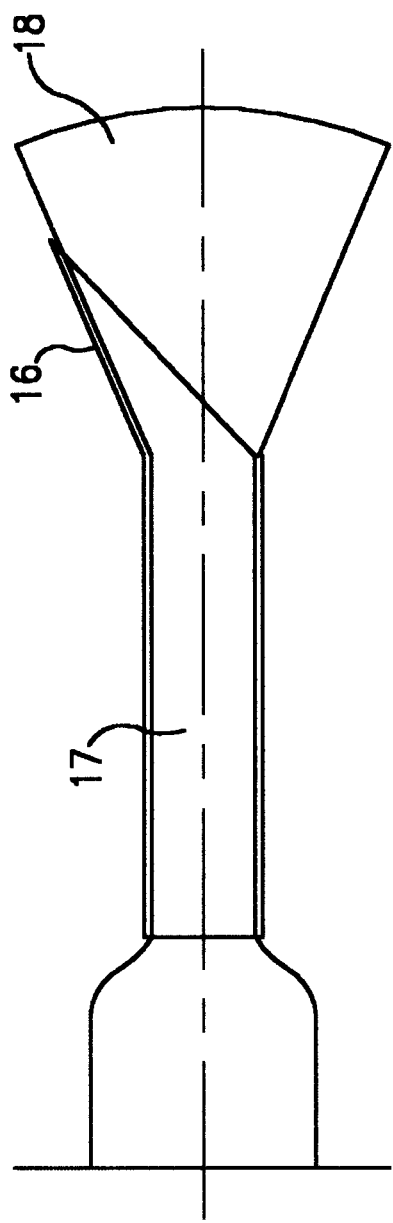
FIG. 6 is a schematic sectional view of an endoprosthesis during expansion with a balloon according to another embodiment of the invention.

FIGS. 5 and 6 show sectional views of an endoprosthesis during expansion with a balloon according to the invention which is supported on the wall of the iliac artery opposite to the treated iliac wall. This balloon presents a cylindrical part (17) prolonged by a flared part (18) of conical form. This flared part ensures optimal expansion of the beveled end of the endoprosthesis. The balloon can be sheathed as shown in FIG. 5 or not sheathed as shown in FIG. 6.

Figure 7:
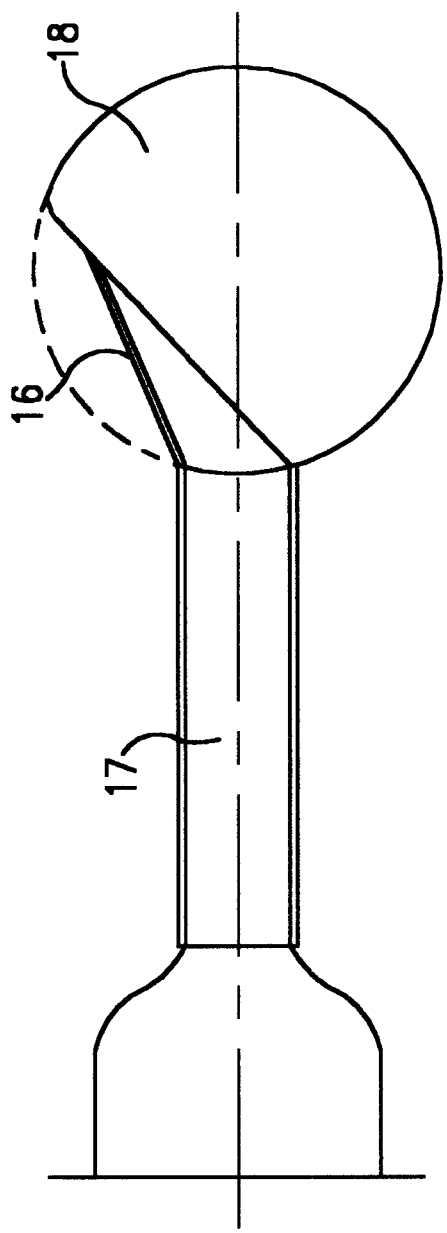
FIG. 7 is a schematic sectional view of an endoprosthesis during expansion with a balloon according to yet another embodiment of the invention.

FIG. 7 shows a section view of an endoprosthesis during expansion with a balloon according to another variant of the invention. The flared part (18) is of spherical form and ensures good support of the beveled end (16) on the interior walls.

The invention also concerns a balloon for the expansion of an endoprosthesis configured so as to exhibit asymmetrical inflation.

According to an embodiment of implementation, the balloon according to the invention has a generally cylindrical form extended at one of the ends by a divergent part. According to another embodiment, it presents a sheathed flared end. According to yet another embodiment, it presents an end of conical form.

Although this invention has been described with reference to specific forms of apparatus and method steps, it will be apparent to one of ordinary skill in the art that various equivalents may be substituted, the sequence of steps may be varied, and certain steps may be used independently of others, all without departing from the spirit and scope of the invention defined in the appended claims.

What is claimed is:

1. An assembly for treatment of a vascular aneurysm in a vessel that intersects another vessel at an oblique angle; said vessel having a neck portion which is short or oblique, said assembly comprising an endoprosthesis having a beveled end and an expansion balloon which has a generally cylindrical shape adapted for asymmetrical inflation, wherein the beveled end is angled to be substantially supplementary to the oblique angle between said vessel and said another vessel, thereby compensating for said short or oblique neck portion.

2. An assembly for treatment of a vascular aneurysm in a vessel that intersects another vessel at an oblique angle; said vessel having a neck portion which is short or oblique, said assembly comprising an endoprosthesis having a beveled end and an expansion balloon which has a generally cylindrical shape adapted for asymmetrical inflation, wherein the beveled end is angled to be substantially supplementary to the oblique angle between said vessel and said another vessel, thereby compensating for said short or oblique neck portion, wherein the balloon is elongated by a divergent part.

3. An assembly for treatment of a vascular aneurysm in a vessel that intersects another vessel at an oblique angle; said vessel having a neck portion which is short or oblique, said assembly comprising an endoprosthesis having a beveled end and an expansion balloon which has a generally cylindrical shape adapted for asymmetrical inflation, wherein the beveled end is angled to be substantially supplementary to the oblique angle between said vessel and said another vessel, thereby compensating for said short or oblique neck portion, wherein the balloon has a sheathed flared end.

4. An assembly for treatment of a vascular aneurysm in a vessel that intersects another vessel at an oblique angle; said vessel having a neck portion which is short or oblique, said assembly comprising an endoprosthesis having a beveled end and an expansion balloon which has a generally cylindrical shape adapted for asymmetrical inflation, wherein the beveled end is angled to be substantially supplementary to the oblique angle between said vessel and said another vessel, thereby compensating for said short or oblique neck portion, wherein the balloon has a conically shaped end.

5. An assembly for treatment of a vascular aneurysm in a vessel intersecting another vessel at an oblique angle, said vessel having a neck portion which is short or oblique, said assembly comprising an endoprosthesis having a beveled end relative to an axis longitudinally extending along a frame and an expansion balloon which has a generally cylindrical shape adapted for asymmetrical inflation, wherein the beveled end is at an angle substantially supplemental to said oblique angle between said vessel and said another vessel, and said beveled end has a front plane which is substantially not perpendicular to an axial line extending through said vessel, thereby compensating for said short or oblique neck portion.

6. A method of treating a vascular aneurysm comprising steps of:

1) locating the aneurysm in a vessel;
2) determining a displacement angle of the vessel containing the aneurysm with respect to an intersecting vessel;
3) adapting a beveled end of an endoprosthesis to have an angle supplementary to said displacement angle; and
4) implanting said endoprosthesis such that the beveled end is substantially parallel to the intersecting vessel.

7. The method of claim 6 further comprising the step of:

asymmetrically inflating a balloon within the endoprosthesis such that said beveled end is firmly affixed to the vessel wall.

* * * * *